(12) United States Patent
Stever et al.

(10) Patent No.: US 10,617,825 B2
(45) Date of Patent: Apr. 14, 2020

(54) DRUG DELIVERY DEVICE

(71) Applicant: SANOFI-AVENTIS DEUTSCHLAND GMBH, Frankfurt am Main (DE)

(72) Inventors: Tobias Stever, Frankfurt am Main (DE); Ngoc-Jane Lam, Frankfurt am Main (DE); Ulrik Jakobi, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 429 days.

(21) Appl. No.: 15/320,655

(22) PCT Filed: Jun. 25, 2015

(86) PCT No.: PCT/EP2015/064356
§ 371 (c)(1),
(2) Date: Dec. 20, 2016

(87) PCT Pub. No.: WO2015/197755
PCT Pub. Date: Dec. 30, 2015

(65) Prior Publication Data
US 2017/0143907 A1 May 25, 2017

(30) Foreign Application Priority Data

Jun. 27, 2014 (EP) .................................. 14174641

(51) Int. Cl.
*A61M 5/315* (2006.01)
*A61M 5/24* (2006.01)
*A61M 5/20* (2006.01)

(52) U.S. Cl.
CPC .......... *A61M 5/31543* (2013.01); *A61M 5/20* (2013.01); *A61M 5/24* (2013.01);
(Continued)

(58) Field of Classification Search
CPC ................ A61M 5/24; A61M 5/31543; A61M 5/31511; A61M 5/315; A61M 5/31535;
(Continued)

(56) References Cited

U.S. PATENT DOCUMENTS

2013/0324936 A1 12/2013 Heald et al.
2016/0287799 A1* 10/2016 Blancke ............ A61M 5/31543

FOREIGN PATENT DOCUMENTS

CN        103648553      3/2014
JP        2013-506442    2/2013
(Continued)

OTHER PUBLICATIONS

International Search Report and Written Opinion in International Application No. PCT/EP2015/064356, dated Sep. 8, 2015, 10 pages.
(Continued)

*Primary Examiner* — Bhisma Mehta
*Assistant Examiner* — Nidah M Hussain
(74) *Attorney, Agent, or Firm* — Fish & Richardson P.C.

(57) ABSTRACT

A drug delivery device (1) is provided comprising a housing (2), a cartridge holder (3) which is adapted and arranged for receiving a cartridge (4) for holding a plurality of doses of a drug (5), wherein the cartridge holder (3) is removable from the housing (2) to enable an exchange of the cartridge (4), a piston rod (9) adapted and arranged to be moved from an initial position towards an end position for dispensing a dose of drug (5) from the device (1) and to be moved from the end position back towards the initial position to perform a reset operation of the device (1), and at least one resilient member (20, 25). The at least one resilient member (20, 25) is in direct mechanical contact with the piston rod (9) and the resilient member (20, 25) is adapted and arranged to prevent an unintentional movement of the piston rod (9) towards the
(Continued)

Figure 1:
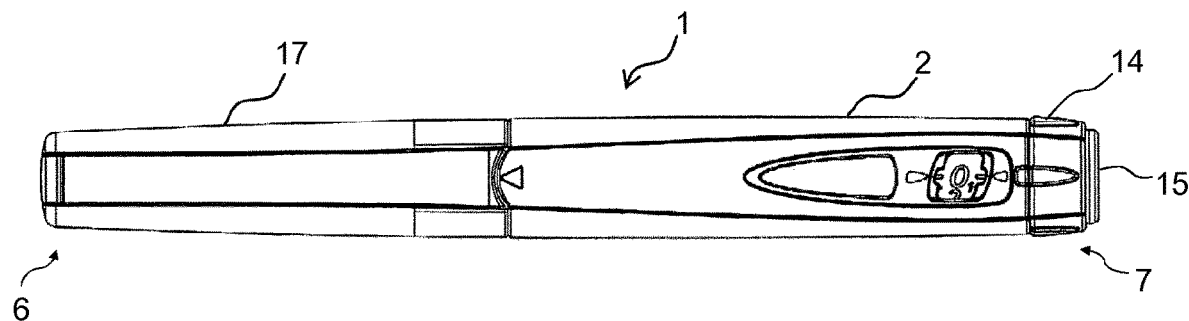
Figure 1:
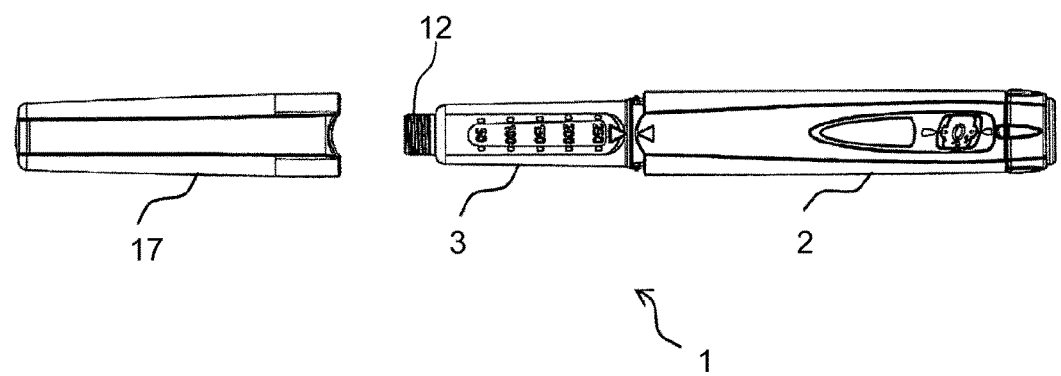

initial position due to mechanical cooperation with the piston rod (9).

17 Claims, 12 Drawing Sheets

(52) U.S. Cl.
CPC ...... *A61M 5/3155* (2013.01); *A61M 5/31511* (2013.01); *A61M 5/31541* (2013.01); *A61M 2005/2026* (2013.01); *A61M 2005/2407* (2013.01)

(58) Field of Classification Search
CPC .......... A61M 5/31501; A61M 5/31551; A61M 5/31553; A61M 5/2422; A61M 2005/2407; A61M 2005/2411; A61M 2005/2433; A61M 2005/2444; A61M 2005/3151

See application file for complete search history.

(56) References Cited

FOREIGN PATENT DOCUMENTS

| JP | 2013-528092 | 7/2013 |
| TW | 201332600 | 8/2013 |
| WO | WO 2008/058666 | 5/2008 |
| WO | WO 2011/039202 | 4/2011 |
| WO | WO 2011/154490 | 12/2011 |
| WO | WO 2012/152666 | 11/2012 |
| WO | WO 2013/068435 | 5/2013 |
| WO | WO 2013/083589 | 6/2013 |
| WO | WO 2013/178602 | 12/2013 |
| WO | WO 2015/197755 | 12/2015 |

OTHER PUBLICATIONS

International Preliminary Report on Patentability in International Application No. PCT/EP2015/064356, dated Dec. 27, 2016, 7 pages.

\* cited by examiner

DRUG DELIVERY DEVICE

CROSS-REFERENCE TO RELATED APPLICATIONS

This application is a U.S. national stage application under 35 USC § 371 of International Application No. PCT/EP2015/064356, filed on Jun. 25, 2015, which claims priority to European Patent Application No. 14174641.2 filed on Jun. 27, 2014, the entire contents of which are incorporated herein by reference.

The present disclosure relates to a drug delivery device.

In a drug delivery device, often, a bung within a cartridge containing a plurality of doses of a drug is displaced by a piston rod. Thereby, a dose of the drug is expelled from the cartridge.

A drug delivery device is described in document WO 2008/058666 A1, for example.

Certain aspects of the present disclosure relate to facilitate provision of an improved drug delivery device.

One aspect relates to a drug delivery device. The device may comprise a housing. The device may further comprise a cartridge holder. The cartridge holder may be connectable, e.g. screwable, to the housing. The cartridge holder may be adapted and arranged for receiving a cartridge for holding a plurality of doses of a drug. The cartridge holder may be removable from the housing to enable an exchange of the cartridge. The device may, thus, be a reusable device. The device may further comprise the cartridge for holding a plurality of doses of a drug. The term "drug", as used herein, preferably means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyhepta-idecanoyl) human insulin.

Exendin-4 for example means Exendin-4(1-39), a peptide of the sequence H His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), wherein the group -Lys6-NH2 may be bound to the C-terminus of the Exendin-4 derivative;

or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2, des Pro36, Pro37, Pro38 [Trp(O2)25, Asp28] Exendin-4 (1-39)-(Lys)6-NH2, H-(Lys)6-des Pro36, Pro37, Pro38 [Trp(O2)25, Asp28] Exendin-4(1-39)-(Lys)6-NH2, H-Asn-(Glu)5-des Pro36, Pro37, Pro38 [Trp(O2)25, Asp28] Exendin-4(1-39)-(Lys)6-NH2, H-(Lys)6-des Pro36 [Met(O)14, Asp28] Exendin-4(1-39)-Lys6-NH2, des Met(O)14 Asp28 Pro36, Pro37, Pro38 Exendin-4(1-39)-NH2, H-(Lys)6-desPro36, Pro37, Pro38 [Met(O)14, Asp28] Exendin-4(1-39)-NH2, H-Asn-(Glu)5-des Pro36, Pro37, Pro38 [Met(O)14, Asp28] Exendin-4(1-39)-NH2, des Pro36, Pro37, Pro38 [Met(O)14, Asp28] Exendin-4 (1-39)-(Lys)6-NH2, H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp (O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2) 25, Asp28] Exendin-4(S1-39)-(Lys)6-NH2, H-Asn-(Glu)5-des Pro36, Pro37, Pro38 [Met(O)14, Trp (O2)25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The cartridge may be connectable, for example screwable, to the housing. Alternatively, the cartridge may be retained in the cartridge holder and the cartridge holder may be connectable to the housing. The cartridge may comprise a bung. The bung is moveably disposed in an interior of the cartridge. The device further comprises a piston rod. The piston rod is moveable with respect to the cartridge. The piston rod may be guided through the housing. The piston rod is adapted and arranged to be moved from an initial position towards an end position for dispensing a dose of the drug from the device and, in particular from the cartridge. The initial position may be that position in which the piston rod is positioned when the device is supplied from the manufacturer. For dispensing a dose, the piston rod may mechanically cooperate with the bung, thereby moving the bung with respect to the cartridge and, thus, expelling the drug from the cartridge. Preferably, the piston rod is in permanent mechanical contact with the bung when a cartridge is loaded within the device.

When the complete amount or almost the complete amount of drug was dispensed from the cartridge, the piston rod is positioned in the end position. The piston rod is adapted and arranged to be moved from the end position back towards the initial position to perform a reset operation of the device. Preferably, the piston rod is moved from the end position towards the initial position after the complete amount of drug was dispensed from the cartridge. The piston rod is moved back into the initial position to prepare the insertion of a replacement cartridge into the device.

The device further comprises at least one resilient member. The resilient member may be a spring member. The resilient member may comprise a spring arm, for example. The resilient member may be adapted and arranged to be in direct mechanical contact with the piston rod. The resilient member may abut, preferably permanently abut, the piston rod.

The at least one resilient member is adapted and arranged to prevent an unintentional movement of the piston rod towards the initial position due to mechanical cooperation with the piston rod. An unintentional movement of the piston rod towards the initial position may occur when the connectable cartridge or the cartridge holder is unintentionally partly removed, e.g. unscrewed, from the device, for example when a user tries to replace a needle assembly on the device. In other words, a movement of the piston rod is for example unintentional, when the piston rod is moved towards the initial position while the cartridge is still loaded within the device. More general, an unintentional movement of the piston rod may be any movement of the piston rod towards the initial position which is not actively triggered by the user.

Preferably, the resilient member mechanically cooperates with the piston rod such that the piston rod cannot be moved back towards the initial position without applying a minimum force against the piston rod in axial direction. In other words, the minimum required force in order to move the piston rod back towards the initial position is determined by a frictional force exerted onto the piston rod by the resilient member that mechanically cooperates with the piston rod in such way that the frictional force represents a mechanical resistance. The piston rod may not be able to move towards the initial position due to its own weight.

In this way, the piston rod always comprises a well-defined position with respect to the bung. In particular, it is prevented to bring the piston rod out of mechanical cooperation with the bung when the cartridge holder containing the cartridge is—unintentionally—partly unscrewed from the device. Only if an axial force is applied onto the piston rod, e.g. when the user intentionally pushes onto the piston rod after the cartridge holder has been detached and the cartridge has been completely removed, the piston rod becomes able to move towards the initial position. In this way, dispensing of an underdose from the cartridge, which may have fatal consequences for a user, can be prevented. Thus, provision of a safe and user-friendly device is facilitated.

According to one embodiment, the resilient member is flexible in the radial direction. The resilient member exerts a radial force, in particular a radially inwardly directed force, onto a peripheral or outer surface of the piston rod such that movement of the piston rod between the initial position and the end position is impeded. Preferably, any movement of the piston rod with respect to the cartridge may be hampered by means of the resilient member. The resilient member may slide along the piston rod when the piston rod is moved between the initial position and the end position. Preferably, the force which is exerted onto the peripheral surface of the piston rod by means of the resilient member does not result in a significant increase of the force which is required for dispensing a dose of the drug, i.e. for moving the piston rod towards the end position. The force which is applied onto the piston rod by means of the resilient member may be adjustable by adjusting an elasticity or spring force of the resilient member, a length of the resilient member, the number of resilient members and/or a diameter of the piston rod. In this way, provision of a flexibly usable drug delivery device is facilitated.

According to one embodiment, the resilient member comprises a free end-face. A free end-face may be an end-face which is not connected to or is not a part of a further component of the device. In this way, a high elasticity of the resilient member is achieved. The free end-face is shaped spoon-like. The free end-face may be rounded. The free end-face may be curved. The free end-face may comprise a convexely curved part or side-face. The free end-face may further comprise a concavely curved part or side-face. The convexely curved part and the concavely curved part may be arranged oppositely to one another. The convex part of the end-face is preferably in direct mechanical contact with the piston rod. The convex part abuts, preferably permanently abuts, the piston rod. In this way, a jamming of the resilient member and the piston rod may be prevented. In particular, it may be prevented that the resilient member gets tilted with a thread arranged on the peripheral surface of the piston rod. In this way, provision of a reliable drug delivery device is facilitated which is less prone to errors.

According to one embodiment, the device comprises two, three or more resilient members. The resilient members may be are arranged symmetrically around the piston rod. In this case the different resilient members may have an equal spring force. In this way, unintentional movement of the piston rod towards the initial position may be effectively prevented. Moreover, the resilient members help to center the piston rod within the device. Alternatively, the different resilient members may have a different spring force as compared to one another. In this case, a symmetric arrangement of the resilient members may be superfluous. Due to the different spring forces of the resilient members, the piston rod may be centered within the device and, further, unintentional movement of the piston rod towards the initial position may be prevented.

According to one embodiment, the device further comprises an interaction member. The interaction member is secured against rotation with respect to the housing. The interaction member and the housing are configured to mechanically cooperate with one another for preventing rotation of the interaction member with respect to the housing. The interaction member may be shaped ring-like. The interaction member may be resilient. The interaction member may be a spring member. The interaction member may be a multispring.

According to one embodiment, the interaction member comprises the resilient member. Preferably, the interaction member may comprise two, three or more resilient members. The resilient member and the interaction member may be integrally formed. The resilient member may be formed out of the interaction member.

According to one embodiment, the interaction member comprises an opening, preferably an inner opening. The piston rod is arranged at least partly within the opening of the interaction member. The piston rod is moveable through the opening between the initial position and the end position. In particular, the interaction member is arranged around the piston rod. The resilient member is adapted and arranged to protrude, e.g. from the interaction member, in a radial inward direction towards the piston rod. The resilient member may be adapted and arranged to protrude in the radial inward direction and into the opening as seen in plan view onto the device. In this way, an inner diameter of the opening may be diminished or reduced. In particular, an area within the device through which the piston rod is moved during operation of the device may be reduced by means of the resilient member. In particular, the resilient member is configured to reduce a diameter of the opening through which the piston rod is guided. In this way, the resilient member mechanically cooperates with the piston rod when the piston rod is moved between the initial position and the end position.

According to one embodiment, the resilient member comprises two end-faces. One endface may be in mechanical contact with the interaction member, for example. Alternatively, the end-face may be in mechanical contact with a further component of the device. In other words, this endface may not be free. The other end-face is free from mechanical contact with the interaction member or with the further component. In other words, said end-face is the previously described free end-face. The free end-face of the resilient member protrudes into the opening of the interaction member—as seen in a plan view onto the device—for mechanically cooperating with the piston rod.

According to one embodiment, the interaction member comprises metal. The interaction member may comprise a carrier. The carrier may be shaped plate-like. The carrier may be circular or approximately circular. The carrier may comprise a shape corresponding to the shape of a diameter, in particular an inner diameter, of the drug delivery device.

The carrier may comprise an inner area comprising the opening. The opening may be stamped out of the inner area of the carrier.

According to one embodiment, the resilient member is formed out of the inner area of the interaction member. The resilient member may protrude from the carrier. Thus, the number of components of the device is kept small. Accordingly, provision of a cost-effective and reliable drug delivery device is facilitated. The resilient member comprises metal. The resilient member may comprise the same metal as the interaction member.

According to one embodiment, the interaction member and, in particular, the carrier comprises at least one securing member. The carrier may comprise two, three or more securing members. With one end, the securing member may be fixed to the carrier. With another end, the securing may be free. The securing member may comprise a spring arm, for example. The resilient member and the securing member may be arranged on opposite sides of the interaction member. The interaction member may comprise a proximal side and a distal side. The distal side may be that side which is arranged closer to a dispensing end of the device. The resilient member may be arranged on the proximal side. The securing member may be arranged on the distal side.

According to one embodiment, the device further comprises a guiding member, e.g. a guide nut. The guiding member may be adapted and arranged to mechanically cooperate with the piston rod for guiding the movement of the piston rod between the initial position and the end position. Due to mechanical cooperation with the guiding member, the piston rod may perform a helical movement through the housing. The securing member may be resiliently mounted on the carrier for engaging with the guiding member. In this way, rotation of the guiding member with respect to the housing may be prevented.

According to one embodiment, the interaction member further comprises a retaining means. The retaining means may be formed as a cantilever-structure with a fixed end and a free end. The fixed end may be fixed onto the carrier. The retaining means may be formed resiliently. The retaining means may comprise a spring arm, for example. The retaining means may comprise a snap feature, e.g. a protrusion. The snap feature may be adapted and arranged for mechanically cooperating with a retaining member of the device for rotationally locking the retaining member with respect to the housing. The interaction member and the retaining member may be adapted and arranged to encompass the guiding member when assembled within the housing of the device. The retaining member may be secured against axial movement with respect to the housing due to mechanical cooperation with the housing. When the cartridge holder is not firmly connected to the housing, the retaining member may be rotatable between a first and a second position. In this way, the securing member may not engage with the guiding member that may rotate with respect to the housing and may lead to the piston rod performing helical movement towards the initial position. When the cartridge holder is firmly connected to the housing, the retaining member may be secured against rotation with respect to the housing due to mechanical cooperation with the interaction member. Consequently, the securing member may engage with the guiding member which becomes prevented from rotating with respect to the housing and the piston rod becomes prevented from moving back towards the initial position, but may be moved towards end position by dispensing.

According to one embodiment, the device further comprises an inner member. The inner member may comprise metal. The inner member may be shaped plate-like. The inner member may comprise a ring-like structure. The inner member may comprise a carrier or base plate. An opening may be provided in an inner area of the carrier. The opening may have a smaller diameter as compared to the opening of the interaction member. The piston rod may be at least partly arranged within the opening of the inner member. The inner member and the resilient member may be integrally formed. Accordingly, the resilient member can be connected or, alternatively, arranged adjacently to the interaction member without being connected to the interaction member by means of the inner member. The resilient member comprises metal. The resilient member comprises the same metal as the inner member.

The resilient member may protrude from the inner member, in particular from the carrier. The inner member and, in particular the carrier, may comprise an inner side-face. The inner side-face may be arranged oppositely to the peripheral surface of the piston rod. The inner member and, in particular the carrier, may comprise an outer side-face. The outer side-face may form an (outer) edge or side of the carrier. The inner side-face may form an (inner) edge or side of the carrier. The resilient member may protrude from the outer side-face towards the inner side-face. This may help to provide a resilient member which comprises a length which is greater than the length of the resilient member being unitarily formed with the interaction member. In this way, the elasticity of the resilient member and the end-face of the resilient member may be optimally adjusted to the size and the diameter of the piston rod.

According to one embodiment, as seen in plan view onto the device, the inner member is arranged at least partly within the opening of the interaction member. As seen in plan view, the inner member at least partly protrudes into the opening of the interaction member. In particular, the resilient member may protrude from the outer side-face and into the opening of the interaction member. In this way, the diameter of the opening of the interaction member may be reduced. The resilient member protrudes into the opening for mechanically cooperating with the piston rod.

According to one embodiment, the resilient member and, in particular the inner member, is connected to the interaction member. In other words, the resilient member and the interaction member may not be integrally formed. Rather, the inner member, which comprises the resilient member, may be engaged with the interaction member. This may help to save development costs for the device as the resilient member can be designed independently from the function of the interaction member. The inner member may be snapped into the opening of the interaction member, for example. Thus, the inner member and the interaction member may be releasably connected. Alternatively, the inner member may be laser-welded to the interaction member. Thus, the inner member and the interaction member may be non-releasably connected.

According to one embodiment, the inner member and the interaction member are arranged adjacently within the housing. The inner member and the interaction member may be arranged to abut one another. However, there may be no connection feature between the inner member and the interaction member. In this way, the resilient member can be designed independently from the function of the interaction member. In particular, a degree of freedom in the construction of the resilient member may be greater as compared to the embodiment where the inner member is connected to the interaction member. Accordingly, a length of the resilient member may be greater as compared to the embodiment where the inner member is connected to the interaction member. Also an outer diameter of the inner member, in particular the whole size, may be greater as compared to the embodiment where the inner member is connected to the interaction member.

The inner member and the interaction member may be arranged in a predetermined position with respect to one another. The predetermined position may be a predetermined rotational or angular position. For arranging the interaction member and the inner member at the predetermined position with respect to one another, an outer shape of the inner member may be equal to or at least similar to an outer shape of the interaction member. In particular, the carriers of the interaction member and the inner member may comprise the same contour or outer shape or at least a similar contour or outer shape. In particular, the interaction member and the inner member may comprise similarly or equally shaped positioning elements. The housing may comprise at least one positioning element, for example two, three or more positioning elements. The positioning element may comprise a notch or groove, for example. The positioning element may be adapted and arranged to receive the inner member and the interaction member for arranging the inner member and the interaction member in the predetermined position with respect to one another.

The inner member may also comprise at least one positioning element, for example two, three or more positioning elements. The number of positioning elements of the inner member may be equal to the number of positioning elements of the housing. The positioning elements of the inner member may be adapted and arranged to mechanically cooperate with the positioning element of the housing. The positioning element may comprise a protrusion, for example. The protrusion may protrude from the carrier of the inner member. The interaction member may comprise at least one positioning element, for example two, three or more positioning elements. The number of positioning elements of the interaction member may be equal to the number of positioning elements of the housing and of the inner member. The positioning element of the interaction member may be adapted and arranged to mechanically cooperate with the positioning element of the housing. The positioning element may comprise a protrusion, for example. The protrusion may protrude from the carrier of the interaction member. An outer shape of the positioning element of the inner member may be equal to an outer shape of the positioning element of the interaction member. The positioning elements of the inner member and the interaction member may be adapted and arranged to mechanically cooperate with the positioning element of the housing such that the inner member and the interaction member are rotationally locked with respect to the housing and with respect to one another.

The resilient member is adapted and arranged to impede the movement of the piston rod towards the initial position when the cartridge holder is only partly removed, e.g. unscrewed, from the housing, which may happen when the user replaces a needle device arranged at an end section of the cartridge holder. By means of the device and especially of the resilient member, the piston rod is kept in arrangement with the bung until the cartridge holder and, thus, the cartridge is completely removed from the device. In this way, a user-friendly and safe drug delivery device is provided.

Of course, features described above in connection with different aspects and embodiments may be combined with each other and with features described below.

Further features and refinements become apparent from the following description of the exemplary embodiments in connection with the accompanying figures.

Figure 2:
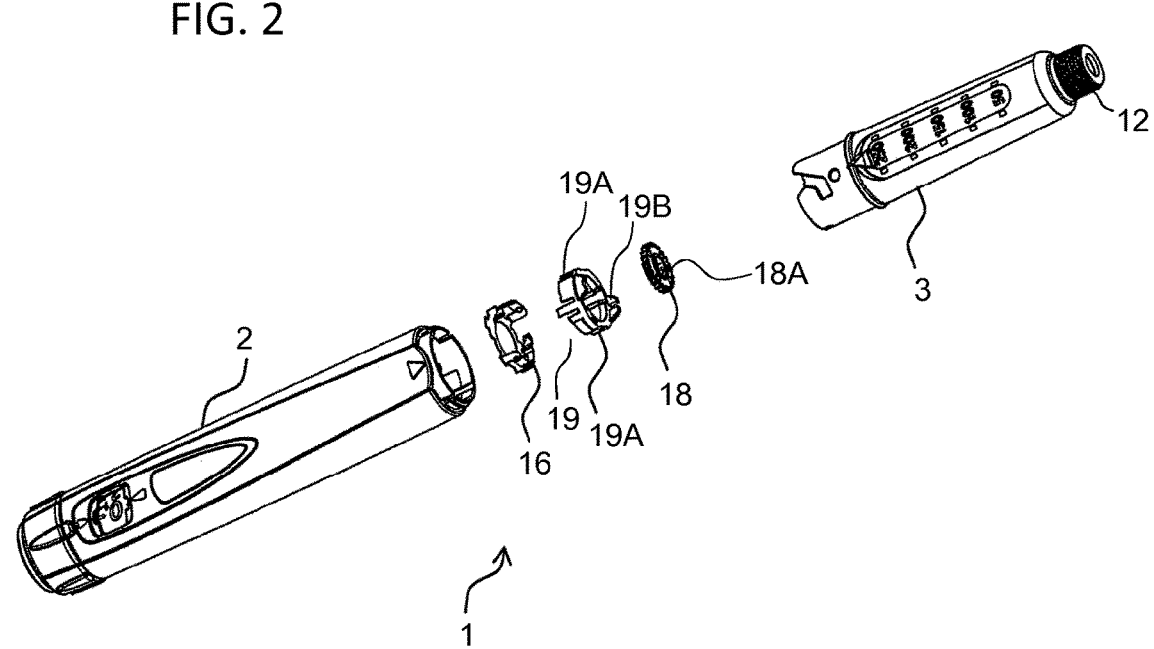
Figure 2A:
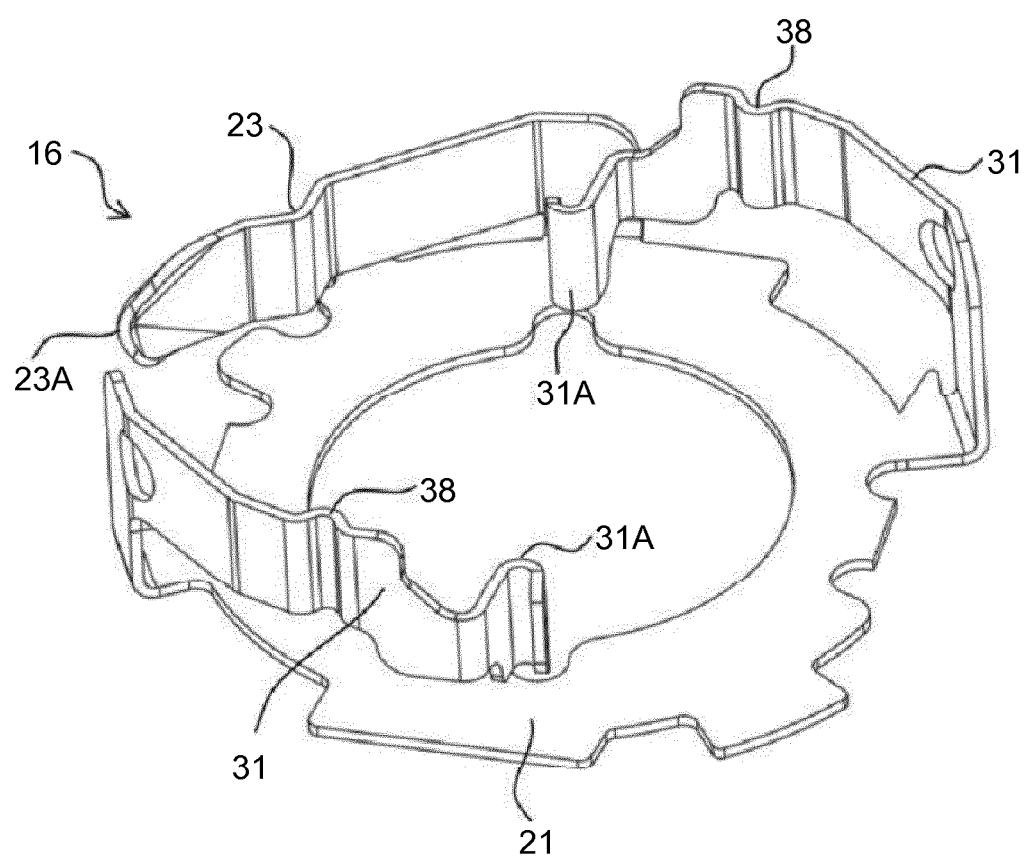
Figure 2B:
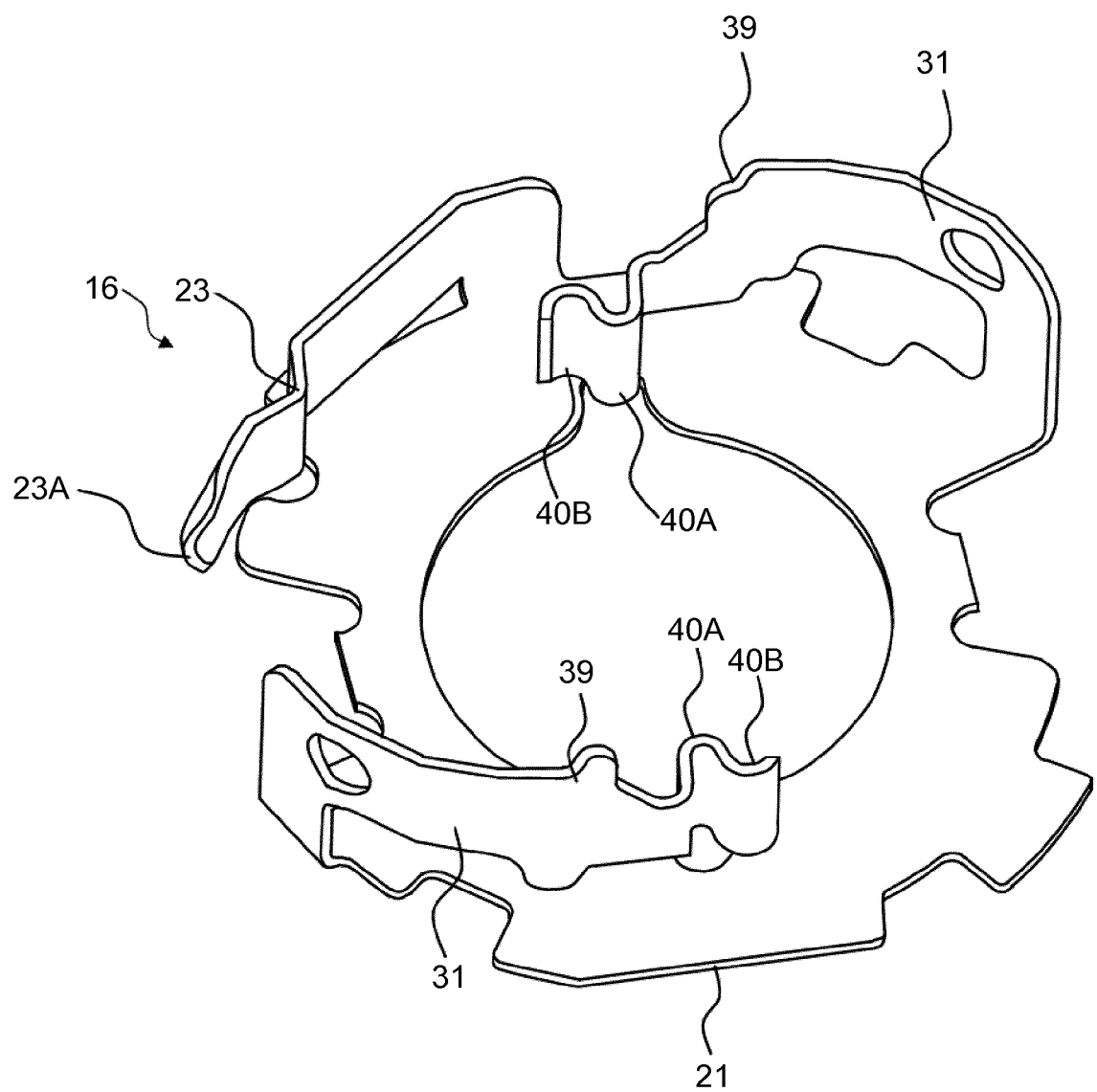
Figure 2C:
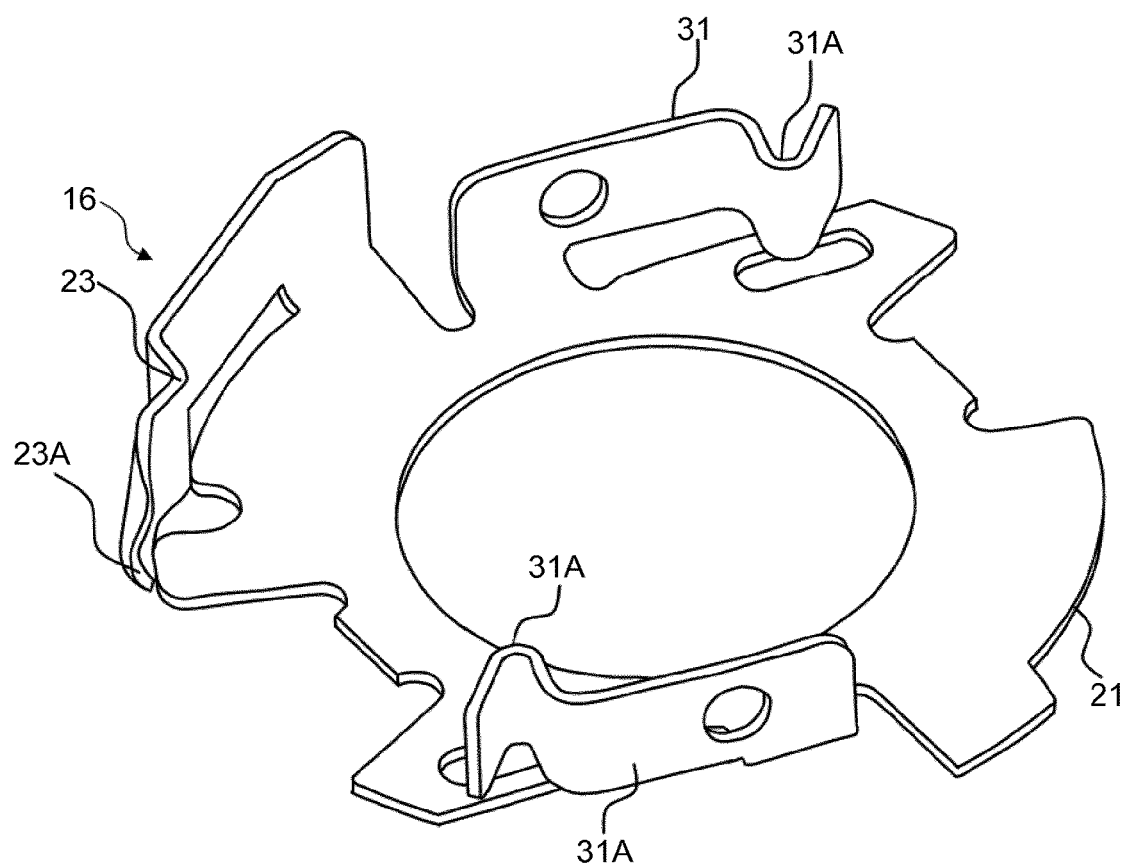
Figure 3:
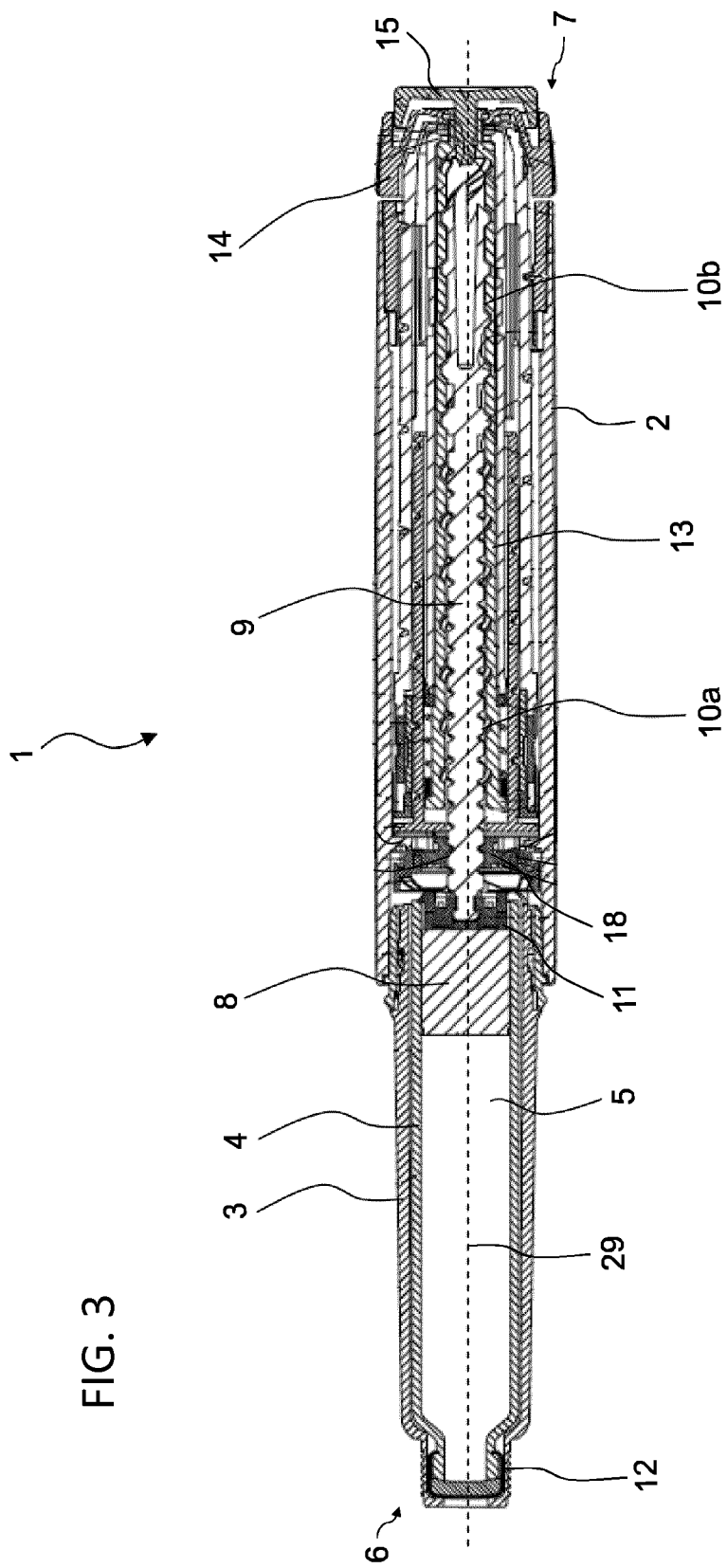
Figure 4:
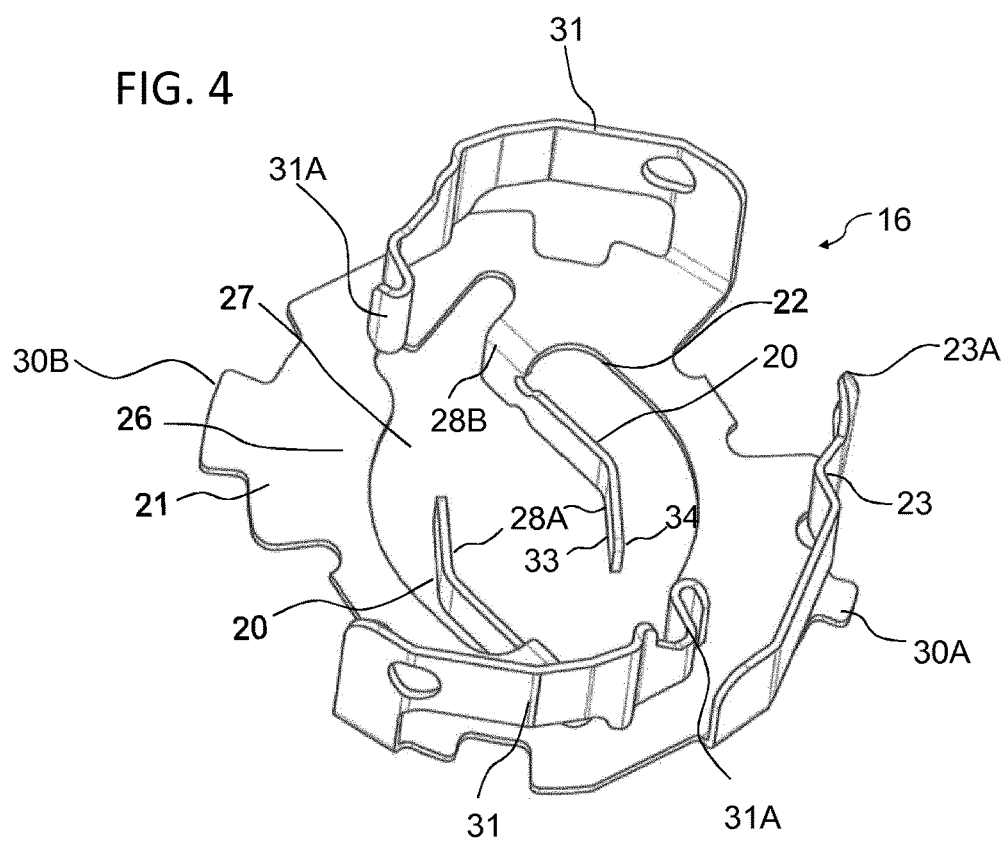
Figure 5:
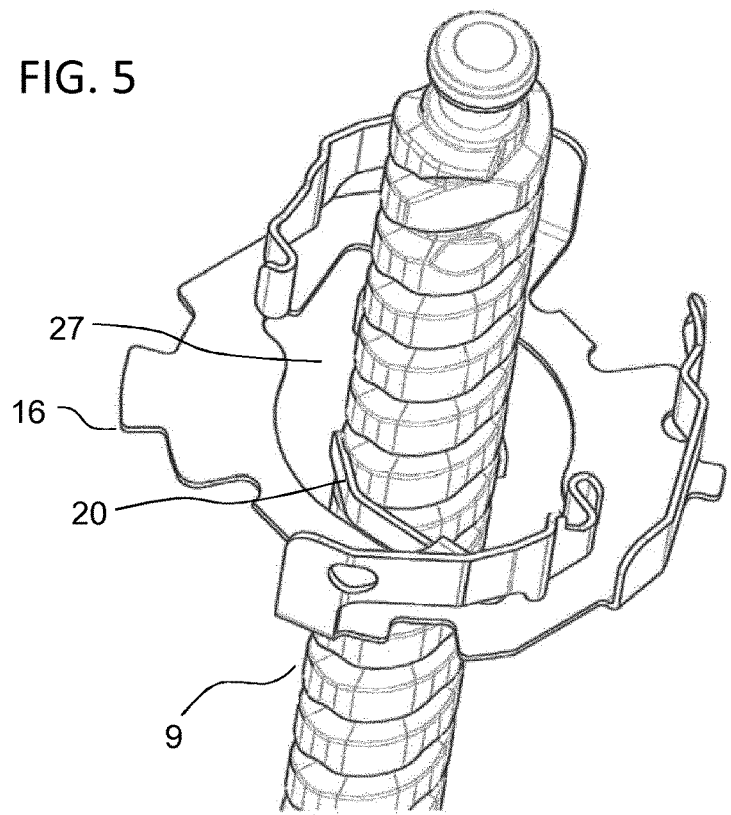
Figure 6:
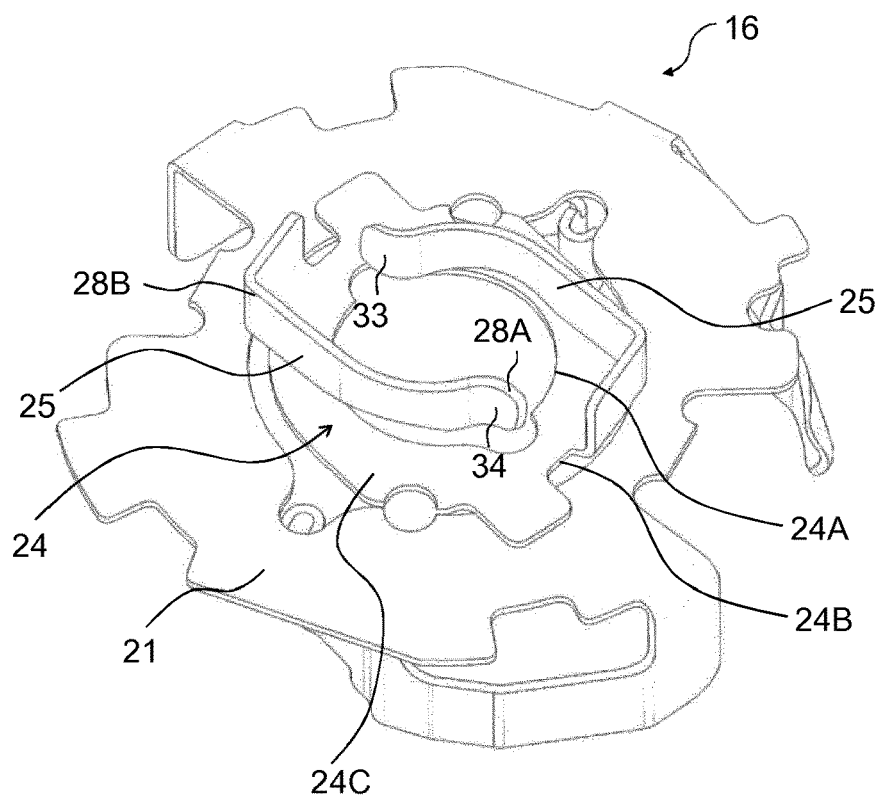
Figure 7:
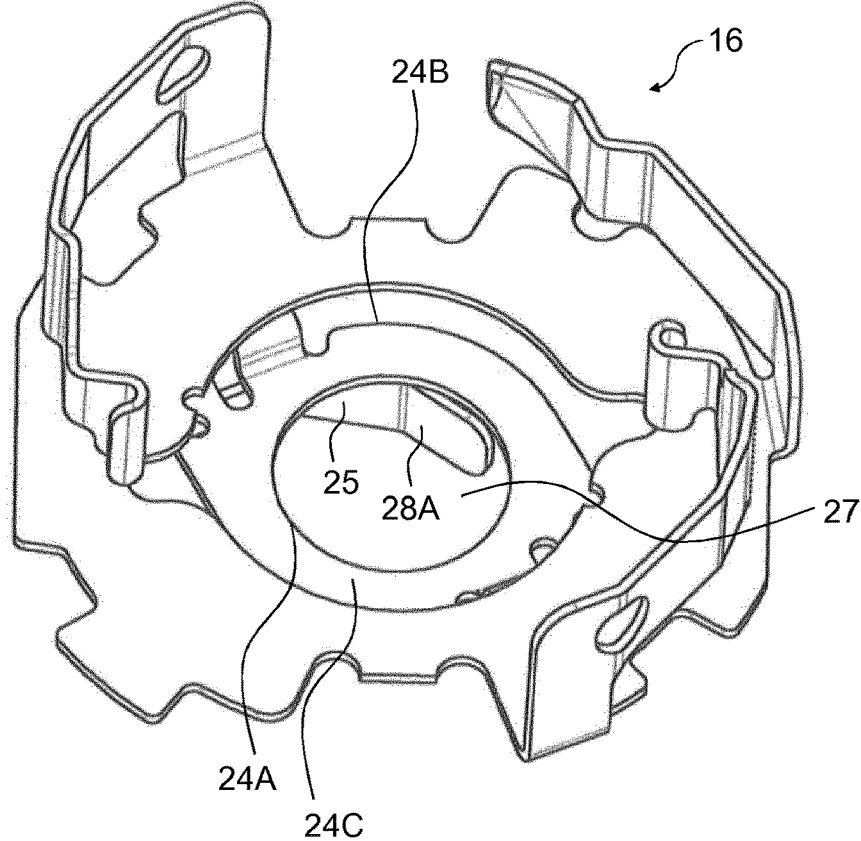
Figure 8:
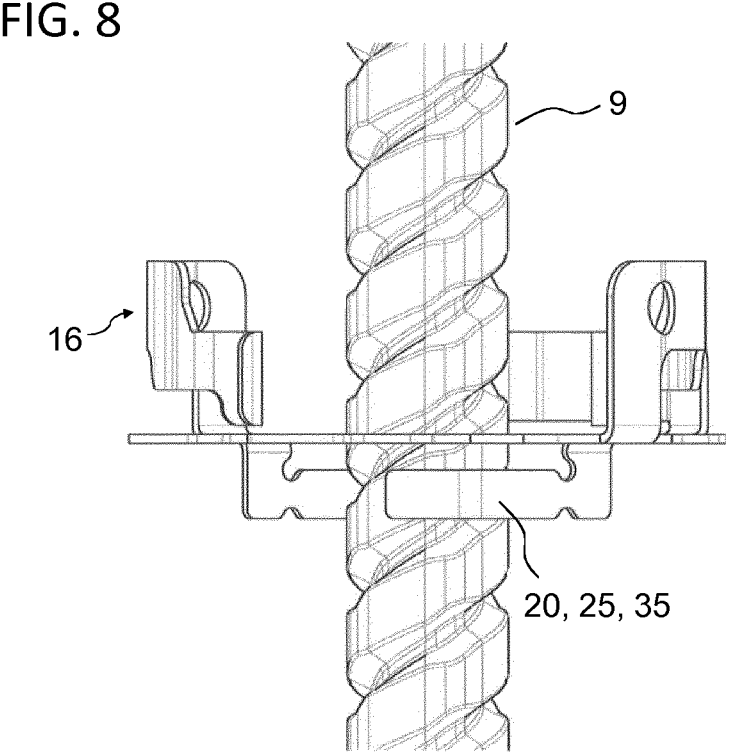
Figure 9:
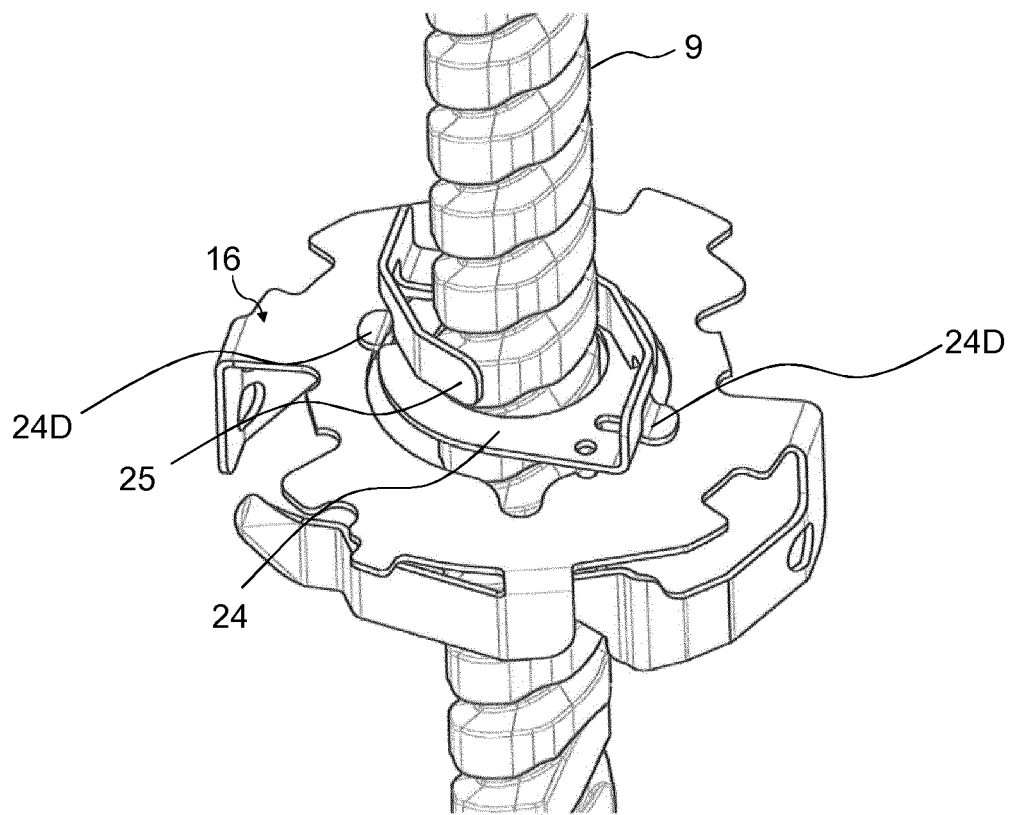
Figure 10:
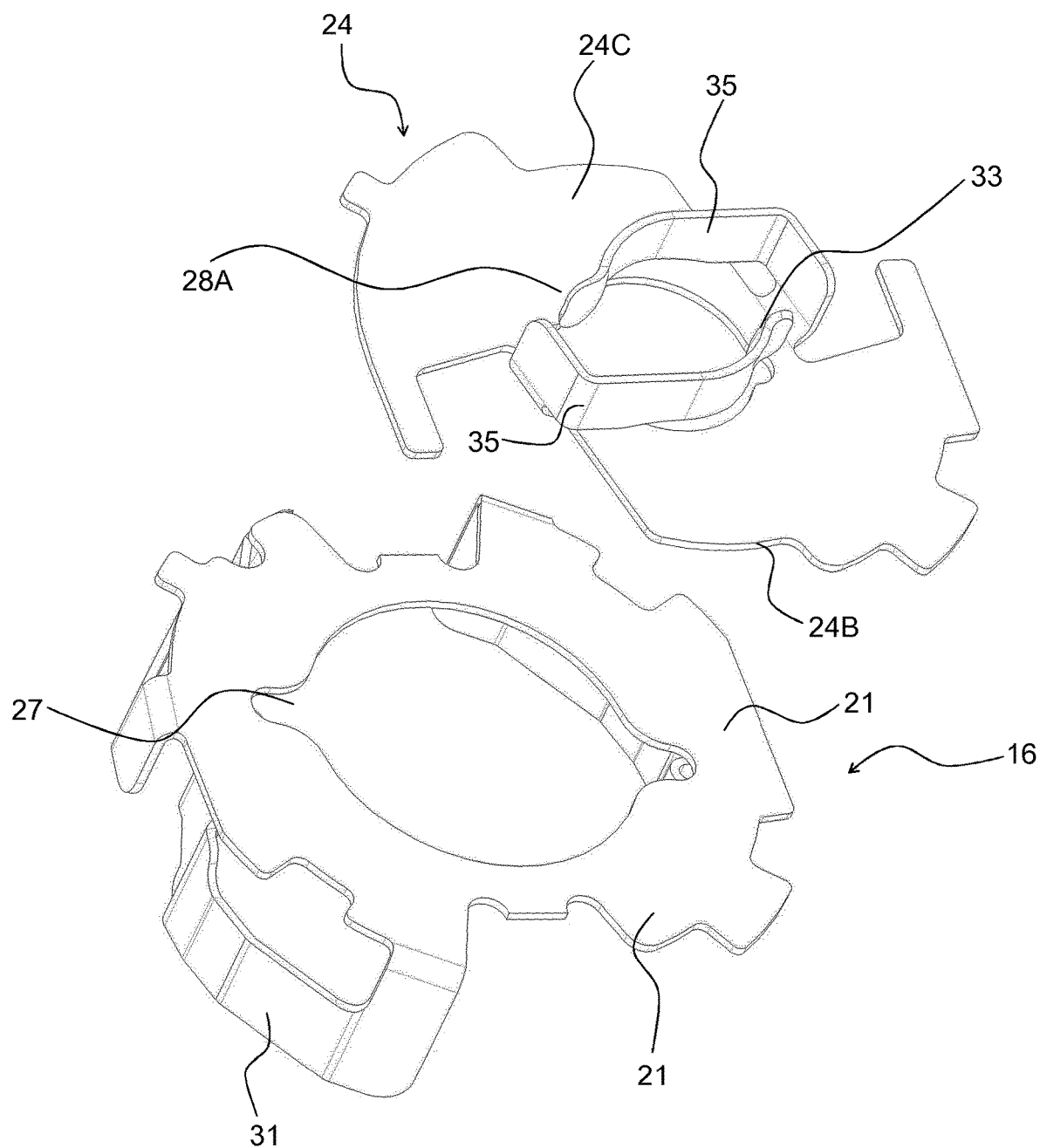
Figure 11:
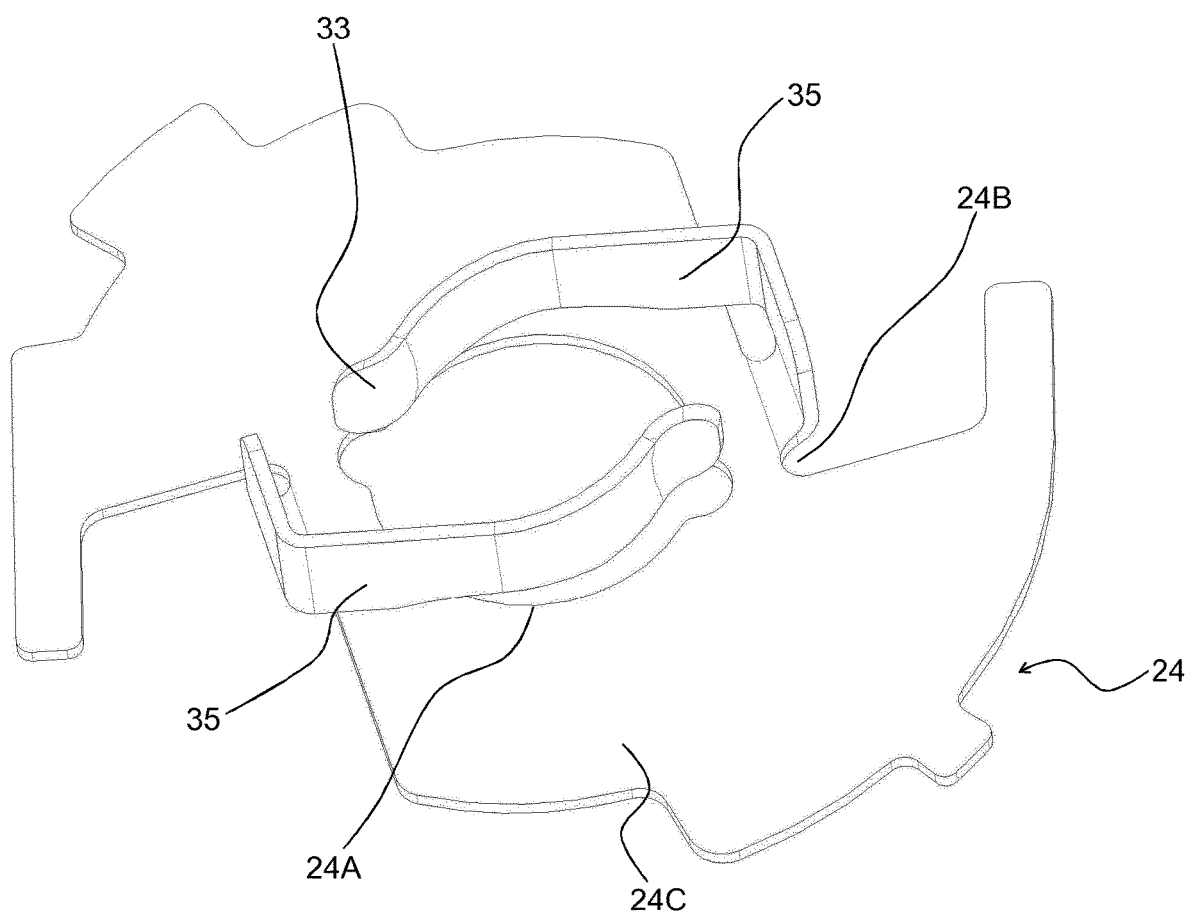
Figure 12:
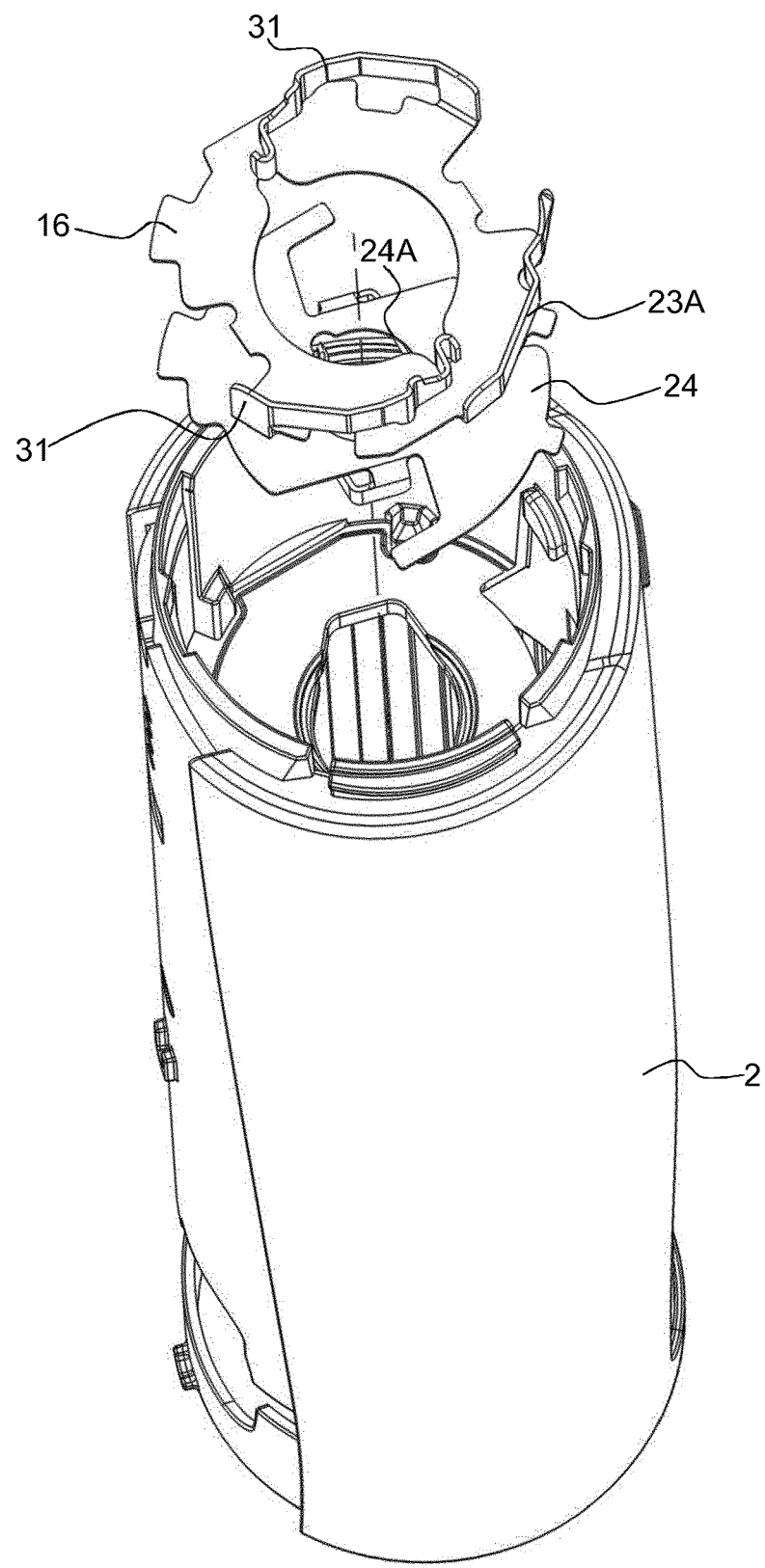
Figure 13:
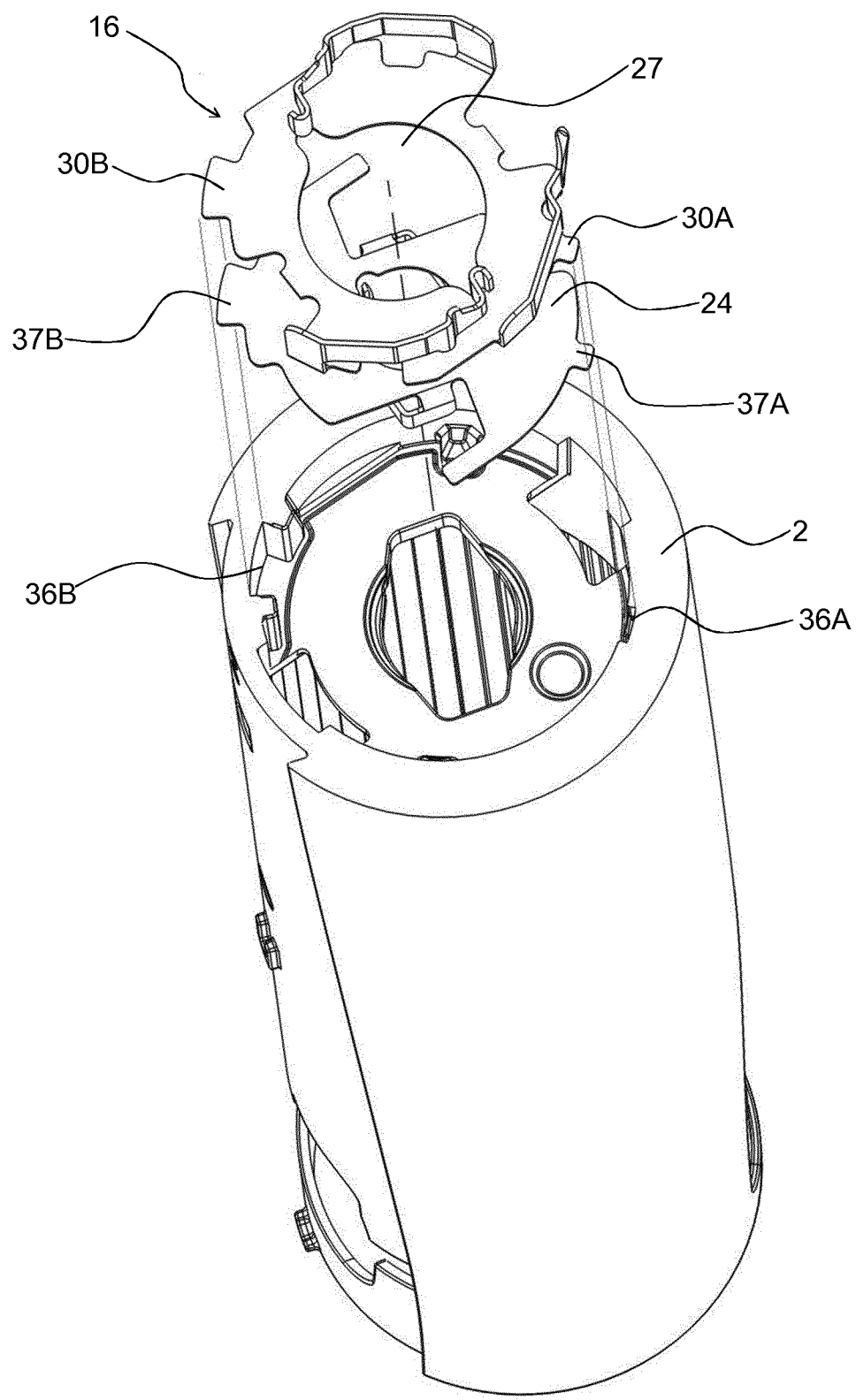

FIG. 1 schematically shows a three-dimensional view of a drug delivery device,

FIG. 2 shows an exploded view of parts of the drug delivery device of FIG. 1,

FIG. 2A shows a three-dimensional view of a part of the drug delivery device of FIG. 1, FIG. 2B shows a three-dimensional view of a part of the drug delivery device of FIG. 1, FIG. 2C shows a three-dimensional view of a part of the drug delivery device of FIG. 1, FIG. 3 shows a sectional side view of the drug delivery device of FIG. 1, FIG. 4 shows a three-dimensional view of a part of the drug delivery device of FIG. 1 according to a first embodiment, FIG. 5 shows a three-dimensional view of parts of the drug delivery device of FIG. 1 according to the first embodiment, FIG. 6 shows a three-dimensional view of a part of the drug delivery device of FIG. 1 according to a second embodiment, FIG. 7 shows a three-dimensional view of a part of the drug delivery device of FIG. 1 according to the second embodiment, FIG. 8 shows a three-dimensional view of parts of the drug delivery device of FIG. 1, FIG. 9 shows a three-dimensional view of parts of the drug delivery device of FIG. 1 according to the second embodiment, FIG. 10 shows a three-dimensional view of a part of the drug delivery device of FIG. 1 according to a third embodiment, FIG. 11 shows a three-dimensional view of a part of the drug delivery device of FIG. 1 according to the third embodiment, FIG. 12 shows a three-dimensional view of a part of the drug delivery device of FIG. 1 according to the third embodiment, FIG. 13 shows a three-dimensional view of a part of the drug delivery device of FIG. 1 according to the third embodiment.

Like elements, elements of the same kind and identically acting elements may be provided with the same reference numerals in the figures.

In FIGS. 1 to 3 a drug delivery device 1 is shown. The drug delivery device 1 comprises a housing 2. The housing 2 is adapted and arranged for protecting components of the device 1 arranged within the housing 2 from environmental influences.

The drug delivery device 1 and the housing 2 have a distal end 6 and a proximal end 7. The term "distal end" designates that end of the drug delivery device 1 or a component thereof which is or is to be arranged closest to a dispensing end of the drug delivery device 1. The term "proximal end" designates that end of the device 1 or a component thereof which is or is to be arranged furthest away from the dispensing end of the device 1. The distal end 6 and the proximal end 7 are spaced apart from one another in the direction of an axis 29. The axis 29 may be the longitudinal axis or rotational axis of the device 1.

The drug delivery device 1 comprises a cartridge holder 3. The cartridge holder 3 comprises a cartridge 4. The cartridge 4 contains a drug 5, preferably a plurality of doses of the drug 5. The cartridge 4 is retained within the cartridge holder 3. The cartridge holder 3 stabilizes the position of the cartridge 4 mechanically. The cartridge holder 3 is connectable, e.g. by a threaded engagement or by a bayonet coupling, to the housing 2. The cartridge holder 3 and the housing 2 are releasably connected to one another. In an alternative embodiment, the cartridge 4 may be directly connected to the housing 2. In this case, the cartridge holder 3 may be redundant. The drug delivery device 1 may be a pen-type device, in particular a pen-type injector. The device 1 may be a re-usable device, which means that the cartridge 4 can be replaced, in particular during a reset operation, by a replacement cartridge for dispensing a plurality of doses from the replacement cartridge.

A bung 5 is slideably retained within the cartridge 4. The bung 5 seals the cartridge 4 proximally. Movement of the bung 5 in the distal direction with respect to the cartridge 4 causes the drug 5 to be dispensed from the cartridge 4. A needle assembly (not explicitly shown in the Figures) can be arranged at the distal end section of the cartridge holder 3, e.g. by means of an engagement means 12, e.g. a thread. A cap 17 may be secured to the cartridge holder 3 to protect the device 1 and, in particular, the cartridge holder 3 from environmental influences, e.g. when the device 1 is not in use.

The device 1 further comprises a dose setting member 14 and a dose button 15 operated for setting and dispensing a dose of the drug 5. The device 1 comprises a piston rod 9. The piston rod 9 is configured to transfer movement through the housing 2 for expelling a dose of drug 5 from the cartridge 4. The piston rod 9 is moveable between an initial position with respect to the housing 2 and an end position with respect to the housing 2. The initial position may be the position of the piston rod 9 when the device 1 is supplied from the manufacturer. Moreover, the initial position may be the position of the piston rod 9 after a reset operation was performed. The initial position may be the most proximal position of the piston rod 9. The end position may be the position of the piston rod 9 after the complete amount of the drug 5 was dispensed from the cartridge 4. The end position may be the most distal position of the piston rod 9. During operation of the device 1, in particular for dispensing a dose of the drug 5, the piston rod 9 is moved towards the end position.

The piston rod 9 has a distal end, which is arranged nearest to the dispensing end of the device 1. The distal end section of the piston rod 9 comprises a bearing member 11. The bearing member 11 is arranged between the bung 8 and the piston rod 9. The bearing member 11 is configured to reduce damages that may be caused by friction. The bearing member 11 may be part of the piston rod 9. The bearing member 11 may be connected to the piston rod 9. Alternatively, the bearing member 11 and the piston rod 9 may be integrally formed. The bearing member 11 and the bung 8 are in mechanical contact, in particular in abutment, throughout the operation of the device. The bearing member 11 and the bung 8 are in mechanical contact as long as the cartridge 4 or a replacement cartridge is loaded within the device. In other words, the bearing member 11 and the bung 8 are in mechanical contact as long as the cartridge holder 3 is at least partly connected to the housing 2, which is explained in detail in connection with the description of the FIGS. 4 to 9.

The piston rod 9 is configured as a lead screw. The piston rod 9 comprises two threaded sections 10A, 10B. The threaded sections 10A, 10B have opposite senses of rotation. A first threaded section 10A is located at a distal part of the piston rod 9 and a threaded section 10B is located at a proximal part of the piston rod 9. The piston rod 9 and, in particular, the first threaded section 10A, is in threaded engagement with a guiding member 18, e.g. a guide nut. The guiding member 18 comprises a centered hole. Within the centered hole a screw thread is designed. The screw thread is used for being coupled to the piston rod 9 in order to urge the piston rod 9 in a predetermined helical movement through the housing 2 and towards the end position. The piston rod 9 is axially and rotationally moveable towards the end position due to mechanical cooperation with the guiding member 18.

Furthermore, the piston rod 9 and, in particular, the second threaded section 10B is in threaded engagement with a drive member 13. The drive member 13 exerts a force onto the piston rod 9 to cause a movement of the piston rod 9 for delivering a dose of the drug 5 when a user pushes onto the dose button 15.

The device further comprises an interaction member 16. The device 1 further comprises a retaining member 19. The interaction member 16 and the retaining member 19 encompass the guiding member 18 when assembled within the housing 2 of the device 1. The interaction member 16 is positioned within the housing 2 and secured against rotational movement with respect to the housing 2, e.g. by mechanical cooperation of locking or positioning elements 30A, 30B (see FIG. 4) with corresponding locking or positioning elements 36A, 36B, e.g. notches or grooves, of the housing 2 (see FIG. 13). The interaction member 16 is a spring member. The interaction member 16 may be designed as a multispring. The interaction member 16 is shaped ring-like or approximately ring-like. The interaction member 16 comprises a carrier 21 (see FIG. 4). The carrier 21 may be shaped plate-like. The carrier 21 comprises an inner area 26. The inner area 26 comprises an opening 27. The opening 27 is stamped out of the inner area 27. In an operating state of the device 1, i.e. the state when the cartridge holder 3 holding the cartridge 4 is—at least partly—connected to the housing 2 and the device 1 is ready for setting and dispensing a dose, the piston rod 9 is led through the opening 27 (see FIG. 5). In particular, the piston rod 9 is at least partly positioned within the opening 27 for being moved through the opening 27 during operation of the device 1.

The interaction member 16 comprises metal. In particular, the interaction member 16 is formed from metal. The interaction member 16 comprises one, two or more securing members 31. The respective securing member 31 is formed in the carrier 21. The securing member 31 and the carrier 21 are integrally formed. The securing member 31 comprises a spring arm, for example. The securing member 31 is resiliently mounted on the carrier 21 for engaging with the guiding member 18. At the respective free end, the securing member 31 comprises an edge or a hook 31A for engagement with corresponding notches or interspaces 18A of the guiding member 18 (see FIG. 2A). Thus, the securing member 31 may be pivoted on its free ends with the hooks 31A thereon towards the centre of the carrier 21. Thus, the respective securing member 31 may perform a radial movement.

In the embodiment shown in the Figures, the interaction member 16 comprises two securing members 31. The securing members 31 comprise an arm or cantilever arranged on opposite side-faces of the carrier 21. The respective securing member 31 can comprise a cantilever- or leaf spring-structure with a hook, a pawl or an edge for engagement with the structure elements of the guiding member 18 as explained below. With one end, the respective securing member 31 is fixed to the carrier 21 and with the other end the securing member 31 is free. The securing member 31 is configured to take an engaged state in which the securing member 31 is engaged with the guiding member 18 in order to prevent rotation of the guiding member 18 with respect to the housing 2. Moreover, the securing member 31 is adapted and arranged to take a disengaged state, in which the securing member 31 is disengaged from the guiding member 18 in order to allow rotation of the guiding member 18. The retaining member 19 may be rotatable relative to the housing 2 for interaction with the securing member 31 in order to change between the engaged state and the disengaged state of the securing member 31 as described later on in more detail.

Due to mechanical cooperation with the interaction member 16, and in particular, the securing members 31, the guiding member 18 is secured against rotational movement with respect to the housing 2 when the cartridge holder 3 is firmly connected to the housing 2, which is explained later in more detail. This means that, as long as the cartridge holder 3 is firmly connected to the housing 2, i.e. it is not partly unscrewed from the housing 2, the guiding member 18 is not rotatable and, hence, mechanical cooperation between the guiding member 18 and the piston rod 9 prevents movement of the piston rod 9 towards the initial position. Thus, when the cartridge holder 3 is firmly connected to the housing 2, unintentional movement of the piston rod 9 towards the initial position is prevented due to mechanical cooperation with the guiding member 18.

The retaining member 19 is a ring-shaped member. The retaining member 19 comprises one or more radial recesses. The securing members 31 may be circumferentially arranged on at least a part of the exterior of the interaction member 19. The securing members 31 may pass the radial recesses of the retaining member 19 in order to engage with the guiding member 18. Preferably, the securing members 31 may be resilient or resiliently mounted such that they are tensioned in radial direction towards the longitudinal axis of the device 1. This has the effect that during the disengaged state of the securing members 31, the retaining member 19 holds the securing members 31 out of engagement with the guiding member 18, whereby for switching into the engaged state of the securing members 31, the retaining member 19 releases the securing members 31 such that the securing members 31 may be urged to pass the recesses of the retaining member 19 caused by spring forces and may engage with the guiding member 18.

Moreover, the retaining member 19 provides a ramp-shaped exterior surface (not explicitly shown in the Figures) providing two ramps arranged at opposite sides of the exterior of the retaining member 19. The ramps are angled ramps providing a transition from a broader diameter to a narrowed diameter of the exterior of the retaining member 19. The ramps are arranged substantially at the positions of the corresponding radial recesses. The ramps are designed in order to enable the securing member 31 to slide along the exterior surface of the retaining member 19 from the broader part to the narrowed part and to perform a radial movement towards the center of the retaining member 19 when reaching the narrowed diameter of the retaining member 19.

In one embodiment (see FIG. 2A), the securing members 31 can provide protrusions 38 which are molded on the cantilever-formed securing members 31 and which are directed towards the centre of the carrier 21. The protrusions 38 are designed for sliding along the ramps on the exterior of the retaining member 19.

A second embodiment (see FIG. 2B) differs from the first embodiment in that the free ends of the cantilever-formed securing members 31 are bent such that an edge is provided forming protrusions 39 for engagement with a part of the retaining member 19 in order to actuate the securing members 31. Moreover, the respective free ends of the cantilever-formed securing members 31 provide a sinusoidal shape with at least two reverse loops 40A and 40B, wherein a first loop 40A is molded towards the axis of the device 1 and forms the hook, edge or pawl 31A for engagement with the guiding member 18 and wherein a second loop 40B is molded away from the axis of the device 1 and finishes in the free end of the securing member 31. The second loop 40B is designed to at least partially contact with a part of the retaining member 19 in the engaged state of the securing members 31, i.e. when the securing members 31 are actuated by the retaining member 19 and engage with the guiding member 18. In particular, in the engaged state, the second loop 40B may be tangentially arranged with respect to a corresponding part of the retaining member 19, thereby providing for a smooth contact with the retaining member 19. This embodiment may provide for a save engagement and contact between the securing members 31 and the retaining member 19 without the risk of any damage of the retaining member 19 due to scratching of a sharp edge of a free end of the securing members 31 on the retaining member 19 during torsional moments.

A third embodiment (see FIG. 2C) differs from the first and second embodiments in that the securing members 31 with their cantilevers are arranged such that the interaction of the retaining member 19 and the securing members 31 works in opposite manner according to the principle of the embodiments of FIGS. 2A and 2B. That means the resilient securing members 31 are tensioned in radial direction away from the axis of the carrier 21 such that spring forces may urge the securing members 31 away from the axis of the assembly for disengagement from the guiding member 18. That means, the retaining member 19 may engage with the securing members 31 in order to urge the securing members 31 in radial direction towards the axis and into engagement with the guiding member 18 oppositely to the spring forces of the tensioned securing members 31. On the contrary, when the securing members 31 are to be brought in the disengaged state, the retaining member 19 may release the securing members 31 such that the securing members 31 are urged in radial direction away from the center axis of the device due to the spring forces of the securing members 31.

The retaining member 19 is secured against axial movement with respect to the housing 2 due to mechanical cooperation with the housing 2. When the cartridge holder 3 is not firmly connected to the housing 2, the retaining member 19 is rotatable between a first and a second position. When the cartridge holder 3 is firmly connected to the housing 2, the retaining member 19 is secured against rotation with respect to the housing 2 due to mechanical cooperation with the interaction member 16. For this purpose, the retaining member 19 comprises a snap feature 19A. The snap feature 19A may comprise a protrusion. The snap feature 19A may be shaped wedge-like.

The interaction member 16 comprises a retaining means 23A. The retaining means 23A is formed as a cantilever-structure with a fixed end and a free end. The retaining means 23A is formed resiliently. The retaining means 23A comprises a spring arm. The fixed end of the retaining means 23A is fixed on the carrier 21. The fixed end of the retaining means 23A protrudes from the carrier 21. The free end points substantially in a tangential direction with respect to the carrier 21. The retaining means 23A comprises a snap feature 23 (see FIG. 4), e.g. a protrusion. The snap feature 19A of the retaining member 19 is configured to interact with the corresponding snap feature 23 of the interaction member 16 for rotationally locking the retaining member 19 with respect to the housing 2 in the locked state of the device 1.

The retaining member 19 further comprises a coupling member 19B. The coupling member 19B comprises protrusions protruding in the distal direction from the retaining member 19. The coupling member 19B is provided for interaction and engagement with a corresponding coupling member (not explicitly shown) of the cartridge holder 3. When the coupling members mechanically cooperate, the retaining member 19 is rotationally locked to the cartridge holder 3. The retaining member 19 can be operated, e.g. rotated, by mechanical cooperation of the coupling members. The retaining member 19 is rotatable during a mounting and unmounting movement of the cartridge holder 3, when said cartridge holder 3 is assembled to or at least partly detached from the housing 2.

When the cartridge holder 3 is rotated for being released from the device 1, the securing member 31 is brought out of mechanical cooperation with the guiding member 18 due to the previously described interaction with the retaining member 19. This allows the guiding member 18 to be rotated with respect to the interaction member 16. When the guiding member 18 is allowed to rotate with respect to the housing 2, the piston rod 9 is moveable towards the initial position for performing the reset operation. In other words, axial movement of the piston rod 9 in the proximal direction into the initial position is possible when the guiding member 18 is free to rotate relatively to the housing 2, thus enabling a helical movement of the guiding member 18 with respect to the piston rod 9 irrespective of the position and movement of the piston rod 9 with respect to the housing 2.

In conventional devices, it can happen that, when the user replaces the needle assembly attached to the distal end section of the cartridge holder 3, he or she also unintentionally moves, in particular rotates, the cartridge holder 3 with respect to the housing 2. Thus, the cartridge holder 3 is rotated without having the intention to remove the cartridge holder 3 and, thus, the cartridge 4 from the device 1. Movement of the cartridge holder 3, however, results in the guiding member 18 being brought out of engagement with the interaction member 16. Thus, the guiding member 18 is rotatable with respect to the housing and the piston rod 9 is unintentionally, e.g. due to gravitational force, moveable in the proximal direction towards the initial position although one or more doses of the drug 5 are still present in the cartridge 4.

Such a movement of the piston rod 9 must be prevented as it causes the bearing member 11 to be brought out of abutment with the bung 8. If the user then tries to set and deliver a further dose of the drug 5, he may deliver an underdose as the piston rod 9 must be brought into abutment with the bung 8 before the piston rod 9 can shift the bung 8 distally for dispensing the dose. Thus, it is crucial that the piston rod 9 is kept in abutment with the bung 8 throughout the use of the device 1 and, in particular, in the case when the user unintentionally rotates the cartridge holder 3 with respect to the housing 2, thereby partly unscrewing the cartridge holder 3 from the housing 2. For preventing an unintentional movement of the piston rod 9 with respect to the housing 2 towards the initial position, the device 1 comprises at least one resilient member 20, 25, 35 as shown in FIG. 8. The resilient member 20, 25, 35 is adapted and arranged for mechanically cooperating with the piston rod 9, particularly with the first threaded section 10A of the piston rod 9, for preventing said unintentional movement.

FIG. 4 shows a three-dimensional view of a part of the drug delivery device of FIG. 1 according to a first embodiment. FIG. 5 shows a three-dimensional view of parts of the drug delivery device of FIG. 1 according to the first embodiment.

In FIG. 4 two resilient members 20 are shown. However, the device 1 may comprise more than two resilient members 20, e.g. three, four or five resilient members 20. Alternatively, the device 1 may comprise only one resilient member 20. In this embodiment, the resilient member 20 is part of the interaction member 16. The resilient member 20 is firmly connected to the interaction member 16. In particular, the resilient member 20 and the interaction member 16 are integrally formed. The resilient member 20 is formed out of the inner area 26 of the carrier 21 of the interaction member 16. The respective resilient member 20 protrudes from the interaction member 16 in a radial inward direction into the opening 27. The resilient member 20, thus, reduces an inner diameter of the opening 27. In particular, the resilient member 20 protrudes from an inner side-face 22 of the interaction member 16 in the radial inward direction. The inner side-face 22 delimits the opening 27 of the interaction member 16. The resilient members 20 and the previously mentioned securing members 31 are arranged at opposite sides of the carrier 21 as shown in FIG. 4. In particular, the securing members 31 are arranged at a distal face of the carrier 21. The resilient members 20 are arranged at a proximal face of the carrier 21.

The resilient members 20 are configured to exert a force, in particular a radial force, onto the piston rod 9. The respective resilient member 20 comprises a length and a shape such that the resilient member 20 can directly mechanically cooperate with the piston rod 9 and, in particular with the first threaded section 10A. The resilient member 20 is pre-tensioned towards the piston rod 9. The resilient members 20 each comprise a spring arm or cantilever which are arranged on opposite sides of the carrier 21. The resilient members 20 can be arranged symmetrically around the piston rod 9 when the piston rod 9 is led through the opening 27 (see FIG. 5). In this case, the different resilient members 20 may have an equal spring force, respectively. Alternatively, the different resilient members 20 can have a different spring force as compared to one another. In this case, the resilient members 20 are not necessarily arranged symmetrically around the piston rod 9 as long as the piston rod 9 is centered in the opening 27 due to the different spring forces of the resilient members 20.

The respective resilient member 20 comprises two end-faces 28A, 28B. With one end-face 28B, the respective resilient member 20 is fixed to the carrier 21. In other words, the end-face 28B is a non-free end-face. The other end-face 28A of the resilient member 20 is free from mechanical cooperation with the interaction member 16. Accordingly, this end-face 28A is a free end-face. The free end-face 28A protrudes into the opening 27. The resilient members 20 are resiliently mounted on the carrier 21. Thus, the resilient members 20 are pivotable on their free end-faces 28 towards the centre of the opening 27. Thus, the resilient members 20 may perform a radial movement.

The free end-face 28A is shaped spoon-like. The free end-face 28A is curved. In particular, it comprises a convexely and a concavely curved side-face 33, 34. The convex side-face 33 is in direct mechanical contact with the piston rod 9. In particular, it abuts the piston rod 9. When the piston rod 9 is moved during the operation and during the reset of the device 1, the piston rod 9 slides along the free end-face 28A, in particular along the convex side-face 33. Thereby a radially inwardly directed force is exerted onto the piston rod 9. Due to mechanical cooperation with the resilient member 20, movement of the piston rod 9 between the initial position and the end position is impeded. In other words, the respective resilient member 20 mechanically cooperates with the piston rod 9 such that the piston rod 9 is moveable only by exceeding a resistance, in particular by exceeding a frictional force exterted onto the piston rod 9 by means of the resilient member 20. In this way, an unintentional movement of the piston rod 9 towards the initial position as described above can be prevented. Thus, as long as the cartridge 4 is loaded within the device 1, the piston rod 9 is always kept in abutment with the bung 8 by means of the resilient member 20 even if the user accidentally partly unscrews the cartridge holder 3 from the housing 2.

Even if the cartridge holder 3 and, thus, the cartridge 4 is completely removed from the device 1, the resilient member 20 keeps the piston rod 9 in the end position until the user actively pushes the piston rod 9 proximally and into the initial position, i.e. until the user intentionally resets the device 1. Afterwards, the cartridge holder 3 holding a replacement cartridge can be screwed to the housing 2.

FIG. 6 shows a three-dimensional view of a part of the drug delivery device of FIG. 1 according to a second embodiment. FIG. 7 shows a three-dimensional view of a part of the drug delivery device of FIG. 1 according to the second embodiment. FIG. 9 shows a three-dimensional view of parts of the drug delivery device of FIG. 1 according to the second embodiment.

In FIG. 6 two resilient members 25 are shown. However, the device 1 may comprise more than two resilient members 25, e.g. three, four or five resilient members 25. Alternatively, the device 1 may comprise only one resilient member 25. With regard to the general features of the resilient members 25, e.g. the shape (for example, the end-faces 28A, 28B) and the function, it is referred to the description of the first embodiment (FIGS. 4 and 5). In contrast to the resilient member 20 of the first embodiment, the resilient member 25 shown in FIGS. 6, 7 and 9 is not integrally formed with the interaction member 16. Rather, in this embodiment, the resilient member 25 is connected to the interaction member 16, which is described below in detail.

In this embodiment an inner member 24 is provided. The inner member 24 is connected, preferably unreleasably connected, to the interaction member 16. The inner member 24 is laser-welded to the interaction member 16, for example. Alternatively, the inner member 24 may be snapped to the interaction member 16. In this case, the connection between the inner member 24 and the interaction member 16 may be releasable. The inner member 24 comprises metal. The inner member 24 comprises a carrier or base plate 24C. The inner member 24 is shaped ring-like. In other words, the inner member 24 comprises an opening arranged within an inner area of the carrier 24C. The opening may be stamped out of the inner area. The opening may have a smaller diameter as compared to the diameter of the opening 27 of the interaction member 16. When the device 1 is in an assembled state, the piston rod 9 is at least partly arranged within the opening of the inner member 24 (see FIG. 9). According to this embodiment, the inner member 24 is arranged within the opening 27 of the interaction member 16. The inner member 24 may comprise a connecting element 24D, e.g. one or more protrusions. The connecting element 24D is adapted and arranged to firmly connect the inner member 24 to the opening 27, in particular an inner surface of the opening 27 which is arranged oppositely to the piston rod 9, of the interaction member 16. The connecting element 24D is, for example, laser welded to the inner surface of the opening 27. Thus, the inner member 24 reduces the diameter of the opening 27.

The respective resilient member 25 is arranged at the inner member 24. The inner member 24 and the resilient members 25 are integrally formed. The inner member 24 comprises an inner side-face 24A and an outer side-face 24B. The inner side-face 24A forms an inner face of the carrier 24C. The outer side-face 24B forms an outer face of the carrier 24C. The inner side-face 24A delimits the opening of the inner member 24, as shown in FIGS. 6 and 7. The resilient member 25 is arranged at the outer side-face 24B. The resilient member 25 protrudes from the outer side-face 24B in the radial inward direction. In an alternative embodiment (not explicitly shown in the Figures), the resilient member 25 can also protrude from the inner side-face 24A in the radial inward direction.

The resilient member 25 protrudes into the opening 27 of the interaction member 16 for mechanically cooperating with the piston rod 9. When the resilient member 25 mechanically cooperates with the piston rod 9, it exerts a radially inwardly directed force onto the piston rod 9, thus impeding the movement of the piston rod 9 between the initial position and the end position as described above.

FIGS. 10 and 11 show a three-dimensional view of a part of the drug delivery device 1 of FIG. 1 according to a third embodiment. FIGS. 12 and 13 shows a three-dimensional view of a part of the drug delivery device 1 of FIG. 1 according to the third embodiment.

In FIGS. 10 and 11 two resilient members 35 are shown. However, the device 1 may comprise more than two resilient members 35, e.g. three, four or five resilient members 35. With regard to the general features of the resilient members 35, e.g. the shape (for example the end-faces 28A, 28B) and the function, it is referred to the description of the first embodiment (FIGS. 4 and 5).

Also in this embodiment, the respective resilient member 35 is arranged at the previously described inner member 24. The inner member 24 and the resilient members 35 are integrally formed as described above. The inner member 24 comprises the previously mentioned inner side-face 24A and the outer side-face 24B which delimit the carrier 24C of the inner member 24.

The respective resilient member 35 is arranged at the outer side-face 24B. The resilient member 35 protrudes from the outer side-face 24B in the radial inward direction (see, in particular, FIG. 11). In an alternative embodiment (not explicitly shown in the Figures), the resilient member 35 can also protrude from the inner side-face 24A in the radial inward direction and, thus, towards the piston rod 9.

In contrast to the resilient member 20 of the first embodiment, the resilient member 35 shown in FIGS. 10 to 13 is, accordingly, not integrally formed with the interaction member 16 (see FIG. 11). Further, in contrast to the resilient member 25 of the second embodiment, this resilient member 35 is also not connected to the interaction member 16 (see FIG. 10). In particular, the inner member 24, which comprises the resilient members 35, is not connected to the interaction member 16. Rather, the inner member 24 and the interaction member 16 and, thus, the resilient members 35 and the interaction member 16, are separate components of the device 1, which are not connected to one another but which are only adapted to be positioned adjacently with respect to one another within the housing 2.

The inner member 24 is arranged more proximal with respect to the housing 2 than the interaction member 16 (see FIGS. 12 and 13). The interaction member 16 and the inner member 24 are arranged within the housing 2 such that they mechanically cooperate with one another. In particular, they abut one another when positioned within the housing 2. The interaction member 16 and the inner member 24 are arranged and/or fixed within the housing 2 at a predetermined position with respect to one another within the housing 2 of the device 1. For this purpose, the carrier 24C of the inner member 24 may have a greater outer diameter as compared to the carrier 24C of the inner member 24 of the second embodiment. In particular, the carrier 24C may have an outer diameter which is similar or equal to the outer diameter of the carrier 21 of the interaction member 16. The carriers 21, 24C may have an equal or at least similar contour or outer shape. In particular, the carriers 21, 24C may comprise equally shaped positioning elements 30A, 30B, 37D, 37B. Due to mechanical cooperation of the carriers 21, 24C and the housing 2, the inner member 24 and the interaction member 16 are arranged in the predetermined position with respect to one another.

The carrier 21 of the interaction member 16 comprises the previously mentioned positioning elements 30A, 30B (see FIG. 13). The positioning elements 30A, 30B are arranged on opposite side-faces of the carrier 21. A first positioning element 30A may comprise a smaller width as compared to a second positioning element 30B. In this case, the term "width" denotes an extension of the positioning elements 30A, 30B in a direction perpendicular to the longitudinal axis of the device 1. According to a further embodiment (not explicitly shown in the figures), the carrier 21 may comprise only one positioning element or more than two positioning elements, e.g. three, four or more positioning elements. The positioning elements 30A, 30B each comprise an edge or a protrusion protruding from the carrier 21 in the radial outward direction. The carrier 24C of the inner member 24 comprises two positioning elements 37A, 37B (see FIG. 13). The positioning elements 37A, 37B are arranged on opposite side-faces of the carrier 24C. A first positioning element 37A may comprise a smaller width as compared to a second positioning element 37B. According to a further embodiment (not explicitly shown in the figures), the carrier 24C may comprise only one positioning element or more than two positioning elements, e.g. three, four or more positioning elements. The positioning elements 37A, 37B each comprise an edge or a protrusion protruding from the carrier 24C in the radial outward direction.

The positioning elements 30A, 30B of the interaction member 16 and the positioning elements 37A, 37B of the inner member 24 are equally shaped. In particular, the first positioning elements 30A, 37A comprise a similar or equal shape and outer dimension, in particular width, as compared to one another and the second positioning elements 30B, 37B comprise a similar or equal shape and outer dimension, in particular width, as compared to one another.

The positioning elements 30A, 30B, 37A, 37B are configured to mechanically cooperate with corresponding positioning elements 36A, 36B of the housing 2 (see FIG. 13). The positioning elements 36A, 36B of the housing 2 are arranged on an inner surface of the housing 2. The positioning elements 36A, 36B may comprise a notch or groove, respectively. The notch or groove extends at least partly along the inner surface of the housing 2. A first positioning element 36A may comprise a smaller width than a second positioning element 36B. The first positioning element 36A may be adapted and arranged to receive the first positioning element 30A, 37A of the interaction member 16 and of the inner member 24. The second positioning element 36B may be adapted and arranged to receive the second positioning element 30B, 37B of the interaction member 16 and of the inner member 24.

When the device 1 is assembled, the inner member 24 is rotationally positioned with respect to the housing 2 such that the first positioning element 36A of the housing 2 receives the first positioning element 37A of the inner member 24 and such that the second positioning element 36B of the housing 2 receives the second positioning element 37B of the inner member 24. Then, the inner member 24 is introduced into the housing 2. Thereby, the first positioning elements 36A, 37A mechanically cooperate with one another and the second positioning elements 36B, 37B mechanically cooperate with one another. In particular, the inner member 24 is guided within the housing 2 due to mechanical cooperation of the positioning elements 36A, 36B, 37A, 37B. Afterwards, the interaction member 16 is rotationally positioned with respect to the housing 2 such that the first positioning element 36A of the housing 2 receives the first positioning element 30A of the interaction member 16 and such that the second positioning element 36B of the housing 2 receives the second positioning element 30B of the interaction member 16. Then, the interaction member 16 is introduced into the housing 2 such that the interaction member 16 is arranged adjacently with respect to the inner member 24. Mechanical cooperation of the positioning elements 30A, 30B, 36A, 36B, 37A, 37B rotationally locks the inner member 24 with respect to the housing 2 and the interaction member 16 with respect to the housing 2. Further, due to mechanical cooperation of the positioning elements 30A, 30B, 36A, 36B, 37A, 37B the inner member 24 and the interaction member 16 are arranged in a predetermined, in particular rotational, position with respect to one another. Accordingly, movement of the inner member 24 and, thus, of the resilient member 35, with respect to the interaction member 16 is prevented although the inner member 24 is not connected to the interaction member 16.

Once the interaction member 16 and the inner member 24 are arranged in the predetermined position, the resilient members 35 protrude into the opening 27 of the interaction member 16—as seen in plan view onto the device—for mechanically cooperating with the piston rod 9 (see FIGS. 10, 12 and 13). In other words, the inner member 24 and, in particular the resilient members 35, diminish an inner diameter of the opening 27 as seen in plan view onto the device 1 although, in this embodiment, the inner member 24 is not arranged within the opening 27 of the interaction member 16. In particular, the area within the housing 2 through which the piston rod 9 is moved during operation of the device 1 is reduced by means of the resilient members 35. When the respective resilient member 35 mechanically cooperates with the piston rod 9, it exerts a radially inwardly directed force onto the piston rod 9, thus impeding the movement of the piston rod 9 between the initial position and the end position as described above.

Other implementations are within the scope of the following claims. Elements of different implementations may be combined to form implementations not specifically described herein.

REFERENCE NUMERALS

1 Drug delivery device
2 Housing
3 Cartridge holder
4 Cartridge
5 Drug
6 Distal end
7 Proximal end
8 Bung
9 Piston rod
10A,10B Threaded section
11 Bearing member
12 Engagement means
13 Drive member
14 Dose setting member
15 Dose button
16 Interaction member
17 Cap
18 Guiding member
18A Notch
19 Retaining member
19A Snap feature
20 Resilient member
21 Carrier
22 Inner side-face
23 Snap feature
23A Retaining means
24 Inner member
24A Inner side-face
24B Outer side-face
24C Carrier
24D Connecting element
25 Resilient member
26 Inner area
27 Opening
28A,B End-face
29 Axis
30, 30B Positioning element
31 Securing member
31A Hook
33 Convex part
33 Concave part
34 Resilient member
36A, 36B Positioning element
37A, 37B Positioning element
38 Protrusion
39 Protrusion
40A, 40B Loop

The invention claimed is:
1. A drug delivery device comprising:
a housing;
a cartridge holder adapted to receive a cartridge for holding a plurality of doses of a drug, wherein the cartridge holder is removable from the housing to enable an exchange of the cartridge;
a piston rod adapted to be moved from an initial position towards an end position for dispensing a dose of drug from the drug delivery device and adapted to be moved from the end position back towards the initial position to perform a reset operation of the drug delivery device;
at least one resilient member that is in direct mechanical contact with the piston rod, the at least one resilient member being adapted to prevent an unintentional movement of the piston rod towards the initial position due to mechanical cooperation with the piston rod;
an interaction member secured against rotation with respect to the housing, wherein the piston rod is arranged at least partly within an opening of the interaction member, and wherein the at least one resilient member protrudes in a radial inward direction towards the piston rod and into the opening, wherein the inter- action member comprises a carrier, and wherein the carrier comprises at least one securing member, wherein a first end of the at least one securing member is fixed to the carrier and a second end of the at least one securing member is free; and a guiding member adapted to mechanically cooperate with the piston rod for guiding movement of the piston rod between the initial position and the end position, wherein the at least one securing member is resiliently mounted on the carrier and configured to engage the guiding member.

2. The drug delivery device according to claim 1, wherein the at least one resilient member is adapted to exert a radial force onto the piston rod that impedes movement of the piston rod between the initial position and the end position.

3. The drug delivery device according to claim 1, wherein the at least one resilient member comprises a free end-face, wherein the free end-face comprises a convex part, and wherein the convex part is in direct mechanical contact with the piston rod.

4. The drug delivery device according to claim 1, wherein the at least one resilient member and the at least one securing member are arranged on opposite sides of the interaction member, and wherein the at least one resilient member protrudes from the carrier.

5. The drug delivery device according to claim 1, wherein the at least one resilient member and the interaction member are integrally formed.

6. The drug delivery device according to claim 1, wherein the at least one securing member comprises a spring arm.

7. The drug delivery device according to claim 1, wherein the interaction member comprises a snap feature adapted to mechanically cooperate with a retaining member of the drug delivery device and rotationally lock the retaining member with respect to the housing.

8. The drug delivery device according to claim 1, comprising an inner member, wherein the inner member and the at least one resilient member are integrally formed, wherein the inner member comprises an inner side-face and an outer side-face and wherein the at least one resilient member protrudes from the outer side-face towards the inner side-face.

9. The drug delivery device according to claim 8, wherein the inner member is arranged at least partly within the opening of the interaction member and wherein the at least one resilient member protrudes from the outer side-face and into the opening of the interaction member.

10. The drug delivery device according to claim 8, wherein the inner member is connected to the interaction member.

11. The drug delivery device according to claim 8, wherein the inner member and the interaction member are arranged adjacently within the housing, wherein the housing comprises at least one positioning element adapted to receive the inner member and the interaction member for arranging the inner member and the interaction member in a predetermined position with respect to one another.

12. The drug delivery device according to claim 11, wherein the inner member comprises at least one positioning element and the interaction member comprises at least one positioning element, the at least one positioning element of the inner member and the at least one positioning element of the interaction member being adapted to mechanically cooperate with the at least one positioning element of the housing and rotationally lock the inner member and the interaction member with respect to the housing.

13. The drug delivery device according to claim 1, wherein the at least one resilient member is adapted to mechanically cooperate with the piston rod during a dispensing operation of the drug delivery device such that movement of the piston rod between the initial position and the end position is impeded.

14. The drug delivery device according to claim 1, wherein the at least one resilient member is adapted to mechanically cooperate with the piston rod in a manner such that a minimum force is required in order to move the piston rod back towards the initial position, wherein the minimum force is determined by a frictional force exerted onto the piston rod by the at least one resilient member.

15. The drug delivery device according to claim 1, wherein the at least one resilient member abuts the piston rod.

16. The drug delivery device according to claim comprising the cartridge containing a medicament.

17. The drug delivery device according to claim 16, wherein the medicament comprises a pharmaceutically active compound.

* * * * *

UNITED STATES PATENT AND TRADEMARK OFFICE
CERTIFICATE OF CORRECTION

PATENT NO. : 10,617,825 B2  
APPLICATION NO. : 15/320655  
DATED : April 14, 2020  
INVENTOR(S) : Tobias Stever, Ngoc-Jane Lam and Ulrik Jakobi Page 1 of 1

It is certified that error appears in the above-identified patent and that said Letters Patent is hereby corrected as shown below:

In the Claims

Column 24, Line 39, Claim 16, delete "claim" and insert -- claim 1, --

Signed and Sealed this  
Second Day of June, 2020

Andrei Iancu  
*Director of the United States Patent and Trademark Office*